United States Patent [19]

Oberlander

[11] Patent Number: 6,077,942

[45] Date of Patent: Jun. 20, 2000

[54] PROCESS OF CONTROLLING PARTICLE SIZE OF NAPHTHOQUINONE DIAZIDE ESTERS

[75] Inventor: Joseph E. Oberlander, Phillipsburg, N.J.

[73] Assignee: Clariant Finance (BVI) Limited, Virgin Islands (Br.)

[21] Appl. No.: 08/995,509

[22] Filed: Dec. 22, 1997

[51] Int. Cl.⁷ .................................................. C07C 245/00

[52] U.S. Cl. ............................................................ 534/558

[58] Field of Search .............................. 544/244; 534/558

[56] References Cited

FOREIGN PATENT DOCUMENTS 04013149  1/1992  Japan .

*Primary Examiner*—S. Mark Clardy
*Assistant Examiner*—Alton Pryor
*Attorney, Agent, or Firm*—Andrew F. Sayko, Jr.; Sangya Jain

[57] ABSTRACT

A process for producing a naphthoquinone diazide ester of a phenolic compound that is useful in a photoresist composition, which process comprises providing a naphthoquinone diazide ester solution in an organic polar solvent; adding the resulting naphthoquinone diazide ester solution to a precipitation bath that is maintained at a temperature of from about 0° C. to about −30° C.; and filtering the resulting naphthoquinone diazide ester.

2 Claims, No Drawings

PROCESS OF CONTROLLING PARTICLE SIZE OF NAPHTHOQUINONE DIAZIDE ESTERS

FIELD OF THE INVENTION

The present invention relates to a method for controlling the particle size of naphthoquinone diazide esters of phenolic compounds, by choosing the correct solvent and carefully controlling the precipitation temperature.

BACKGROUND OF THE INVENTION

It is well known in the art to produce positive photoresist formulations such as those described in U.S. Pat. Nos. 3,666,473, 4,115,128, 4,173,470 and 4,550,069. These include alkali-soluble, film forming polyvinyl phenol or novolak resins together with light-sensitive materials (sensitizers), usually a substituted naphthoquinone diazide compound. The resins and sensitizers are dissolved in an organic solvent or mixture of solvents and are applied as a thin film or coating to a substrate suitable for the particular application desired.

The novolak or polyvinyl phenol resin component of these photoresist formulations are soluble in aqueous alkaline solutions, but the naphthoquinone sensitizer acts as a dissolution rate inhibitor with respect to these film forming resins. Upon exposure to actinic radiation of selected areas of the substrate on which the photoresist composition has been coated, the sensitizer undergoes a radiation induced structural transformation and the exposed areas of the coating are rendered much more soluble than the unexposed areas. This difference in solubility rates causes the exposed areas of the photoresist coating to be dissolved when the substrate is exposed to an alkaline developing solution while the unexposed areas are largely unaffected, thus producing a positive relief pattern on the substrate.

An important group of photosensitizers are the condensation products of 1,2-naphthoquinonediazide-4-sulfonic acid or 1,2-naphthoquinonediazide-5-sulfonic acid and polyols. These compounds tend to exhibit superior photospeed and contrast in the mid-UV region of the light spectrum when formulated in photoresist compositions.

The trend in microlithography during the past few years has been an accelerated drive towards smaller geometries. The efforts to achieve these shrinking design rules require intensive efforts by both exposure tool and photoresist manufacturers. Therefore, there is an increasing demand for UV-2 (DEEP-UV) and UV-3 (I-LINE) sensitive photoresist systems. Novolak-containing photoresists are still workable for g-line and i-line type resists. 2,1,5-diazonaphthoquinone sulfonate esters of trihydroxy benzophenones are generally used as photoactive compounds (PAC) for broad band or g-line resists. On the other hand 2,1,4-diazonaphthoquinone esters are more generally suitable for the i-line (365 nm) region of the spectrum.

Synthesis of such a 2,1,5-diazonaphthoquinone ester is normally conducted in a solvent system such as: N-methyl pyrollidone (NMP), acetone, acetonitrile or a mixed solvent system. A base is generally used as a catalyst and also as an acid acceptor. Common organic bases used include pyridine, triethylamine, N-methyl morpholine, dimethyl amino pyridine and mixtures thereof. The processes utilizing such solvent/base systems provide diazonaphthoquinone esters of consistently good quality. However, providing similar quality and consistent particle size for the diazo ester becomes extremely difficult if a similar process is utilized for making a 2,1,4-diazo ester or a 2,1,4-/2,1,5- mixed diazo ester. In addition, making a 2,1,4-diazo ester or a 2,1,4-/2,1,5- mixed diazo ester becomes even more difficult when utilizing a tetrahydroxybenzophenone. The PAC may be precipitated from the reaction solvent after the condensation reaction by adding the reaction mixture to either an aqueous organic solvent, such as methanol or to an aqueous systems that contain an acid, as is well known in the prior art.

SUMMARY OF THE INVENTION

The invention relates to an improved process for controlling the particle size of a diazonaphthoquinone sulfonate ester after synthesis from a diazo sulfonyl chloride and one or more phenolic compounds. When the PAC does not have particles, which are too small in size, it can be processed easily and a well washed product is obtained. When the PAC is not able to be washed well, synthesis by-products and impurities remain in the PAC, and can adversely influence resist performance. More particularly, the present invention relates to a process for making a 2,1,5-diazo ester and a mixed 2,1,4-/2,1,5- diazo esters of a phenolic compound, such as a benzophenone. The present process utilizes an organic polar solvent, such as acetone, propylene glycol methyl ether (PGME), acetonitrile, N-methyl pyrollidone (NMP), dioxane, and gamma-butyrolactone (BLO) and a base which serves as an acid scavenger, such as Dimethylaminopyridine, triethylamine (TEA), Diethylethanolamine (DEEA), 1,4-diazabicyclo (, 2,2}octane (Dabco), N-methylmorpholine (NMM) and Triethanolamine. The preferred temperature of the drowning (precipitation) bath is from about 0° C. to about −30° C., preferably from about −10° C. to about −20° C.

The present process more particularly comprises: A) providing a solution of a naphthoquinone diazide ester of a phenolic compound in an organic polar solvent; B) adding the naphthoquinone diazide ester solution from step A to a precipitation bath maintained at a temperature of from about 0° C. to about −30° C. The subject process provides consistent quality diazonaphthoquinone esters, where the particle size is large enough for easy processing. The process of the present invention can provide diazonaphthoquinone esters with no substantial amount of complex side products. These side products preclude the production of consistently yellow, substantially pure diazonaphthoquinone esters, in comparison to the gray, dark amber to even green color of impure diazo esters. The subject process can be easily controlled and a slight shift in reaction temperature, time, base concentration etc. does not lead to poor quality or inconsistent material. A major shift in the reaction temperature is needed to cause such problems.

The process is cost effective, safe and leads to consistently high quality yellow colored diazo ester material and is applicable for a wide variety of diazo ester compositions. The photosensitizer composition may be obtained by condensing phenolic compounds with a diazo organic acid halide. The diazo and the organic acid halide may be condensed either sequentially or concurrently with a phenolic compound to provide the diazo organic acid ester.

The diazo organic acid halide may preferably be reacted in stoichiometric quantities with one or more of hydroxyl-bearing phenolic compound. However, the phenolic compound need not be completely esterified and less than stoichiometric quantities of the diazo and organic acid halide compound may be condensed with the phenolic compound. The total amount of diazo and organic acid halide reacted with the phenolic compounds should be sufficient to produce a photosensitizer composition capable of inhibiting the dissolution rate of an alkali-soluble resin.

Among the organic acid halides which may be reacted with a 1,2-naphthoquinone-5-sulfonic acid or 1,2-naphthoquinone4-sulfonic acid, to produce the 2,1,4- and 2,1,5-diazonaphthoquinone sulfonyl chloride utilized in the process of the present invention are: an alkyl sulfonyl halide such as methanesulfonyl chloride, ethanesulfonyl chloride, propanesulfonyl chloride, n-butanesulfonyl chloride, dodecanesulfonyl chloride, and the like; arylsulfonyl chlorides such as benzenesulfonyl chloride, naphthalenesulfonyl chlorides, and the like; acyl halides such as acetyl chloride, butanoyl chloride, valeryl chloride, benzoyl chloride, benzoyl bromide, naphthoyl chlorides, and the like. The preferred organic acid halides are lower alkyl sulfonyl halides having 1 to 6 carbon atoms, benzenesulfonyl halides and benzoyl halides. The acid halides may be substituted or unsubstituted.

The acid scavenger may be inorganic, such as sodium carbonate or the like, or an organic amine such as triethylamine, a pyridine or N-methyl morpholine.

The following specific examples will provide detailed illustrations of the method of the present invention. These examples are not intended to limit or restrict the scope of the invention in any way and should not be construed as providing conditions, parameters or values which must be utilized exclusively in order to practice the present invention. Examples 2 and 4 illustrate the process of the present invention. Examples 1 and 3 illustrate the failure of the current conditions.

EXAMPLE 1

96 g solution of 16% PW-292 PAC [Diazo 2,1,4- and 2,1,5- esters of tris 2,2,2-(4-hydroxyphenyl) ethane, approx. 98% esterified with a ratio of 70% diazo 2,1,5- to 2,1,4-] in gamma-butyrolactone (BLO)/acetone (67%/33%) solvent was prepared by mixing the PW-292 PAC with solvent at room temperature until the PAC was totally dissolved. The solution was split into two equal 48 gram portions. 1200 ml of 20% aqueous methanol was prepared and split into two equal portions. To the first portion of aqueous methanol at room temperature was slowly added, with stirring, one portion of the PAC BLO/acetone solution. A suspension/slurry was produced that could not be filtered using a Buchner filter. The suspension/slurry blinded/clogged the filter causing filtration failure.

EXAMPLE 2

A second trial was run wherein the second portion of aqueous methanol from example 1 was cooled to −10° C. and the second portion of PAC BLO/acetone solution from example 1 was slowly added, with stirring. This approach afforded product slurry that was easily filtered using a Buchner filter. The product after filtration was then washed well with deionized (DI) water to remove trace solvents and other contaminants.

EXAMPLE 3

100 g solution of 20% PW-894 PAC (Diazo 2,1,5- Esters of a formaldehyde p-Creosol Novolak resin, av. MWw about 720 and approximately 40% esterified) in acetone was prepared by mixing the PAC with acetone at room temperature until all of the PAC was dissolved. The solution was split into two equal 50 gram portions. 800 ml of 20% aqueous methanol was prepared and split into two equal portions. To the first portion of aqueous methanol, at room temperature, was slowly added, with stirring, one portion of the PAC/acetone solution. A suspension/slurry was afforded that could not be filtered using a Buchner filter. The suspension/slurry clogged/blinded the filter causing filtration failure.

EXAMPLE 4

A second trial was run wherein the second portion of aqueous methanol from example 3 was cooled to −10° C. and the second portion of PAC/acetone solution from example 3 was slowly added, with stirring. This approach afforded a product slurry that was easily filtered using a Buchner filter. The product after filtration was then washed well with DI water to remove trace solvents and other contaminants.

What is claimed is:

1. A process for isolating or purifying a naphthoquinone diazide ester of a phenolic compound which is useful in a photoresist composition, which process consists essentially of;

A. providing a naphthoquinone diazide phendic ester solution in an organic polar solvent, wherein the organic polar solvent is acetone, propylene glycol methyl ether, acetonitrile, N-methylpyrollidone, dioxane, gamma-butyrolactone and mixtures thereof;

B. adding the naphthoquinone diazide ester solution from step A to a precipitation bath that is maintained at a temperature from about ° C. to about −30° C.; and C. filtering the naphthoquinone diazide ester resulting from step B.

2. The process of claim 1 wherein the precipitation bath is maintained at a temperature from about −10° C. to about −20° C.

\* \* \* \* \*